United States Patent
Fagan et al.

(10) Patent No.: US 8,398,711 B2
(45) Date of Patent: Mar. 19, 2013

(54) SPEECH VALVE

(75) Inventors: Michael J. Fagan, Brandesburton (GB); Stephen R. Ell, North Ferriby (GB); Timothy A. Paget, Gillingham (GB); Catherine A. Dobson, Hull (GB); Zahra N. Mahmoud, Bristol (GB)

(73) Assignee: University of Hull, Hull (GB)

( * ) Notice: Subject to any disclaimer, the term of this patent is extended or adjusted under 35 U.S.C. 154(b) by 619 days.

(21) Appl. No.: 12/446,939

(22) PCT Filed: Oct. 18, 2007

(86) PCT No.: PCT/GB2007/003986
§ 371 (c)(1),
(2), (4) Date: Aug. 4, 2009

(87) PCT Pub. No.: WO2008/050093
PCT Pub. Date: May 2, 2008

(65) Prior Publication Data
US 2009/0283098 A1 Nov. 19, 2009

(30) Foreign Application Priority Data
Oct. 24, 2006 (GB) .................................. 0621161.9

(51) Int. Cl.
*A61F 2/20* (2006.01)

(52) U.S. Cl. ........................................................ 623/9

(58) Field of Classification Search ...................... 623/9; 128/207.14–207.16
See application file for complete search history.

(56) References Cited

U.S. PATENT DOCUMENTS

| 5,125,971 | A | 6/1992 | Nonami et al. |
| 6,422,235 | B1 * | 7/2002 | Persson ................... 128/200.26 |
| 7,166,128 | B1 * | 1/2007 | Persson ............................ 623/9 |
| 7,909,868 | B2 * | 3/2011 | Blom ................................ 623/9 |
| 8,211,457 | B2 | 7/2012 | Hossainy et al. |
| 2004/0187941 | A1 * | 9/2004 | Seder et al. ................... 137/855 |
| 2005/0256573 | A1 | 11/2005 | Seder et al. |
| 2006/0287722 | A1 * | 12/2006 | Nelson ............................ 623/9 |
| 2008/0275402 | A1 * | 11/2008 | Schnell ........................ 604/175 |
| 2009/0043386 | A1 * | 2/2009 | Persson ............................ 623/9 |
| 2011/0093071 | A1 * | 4/2011 | Blom ................................ 623/9 |
| 2012/0215306 | A1 * | 8/2012 | Fagan et al. ..................... 623/9 |

FOREIGN PATENT DOCUMENTS

| DE | 102004051679 B3 | 12/2005 |
| EP | 0344107 A1 | 11/1989 |
| EP | 1707156 A1 | 10/2006 |
| JP | 07-048264 | 2/1995 |
| WO | 97/45075 A1 | 12/1997 |
| WO | WO 9745075 A1 * | 12/1997 |
| WO | WO 9810718 A1 * | 3/1998 |

OTHER PUBLICATIONS

International Search Report for PCT/GB2007/003986.

* cited by examiner

*Primary Examiner* — Suzette J Gherbi
(74) *Attorney, Agent, or Firm* — Brooks Kushman P.C.

(57) ABSTRACT

A speech valve comprises a generally cylindrical body and a closure member which is slidably movable within the body between a closed position and an open position. The valve body and the closure member are formed of a rigid, smooth material which is resistant to the growth of biofilm such as a ceramic. A particular suitable ceramic is partially stabilised zirconia. The valve body is provided with an outer sleeve which is provided with radially outward extending annular flanges, which are used to retain the speech valve in a fistula between the oesophagus and the trachea.

14 Claims, 2 Drawing Sheets

SPEECH VALVE

The invention relates to a speech valve having a body and a projection.

Treatment of throat cancer often involves laryngectomy. A laryngectomy results in the trachea being diverted to an opening, or stoma, located at the outside of a patient's throat. The natural opening between the trachea and the Oesophagus is closed so that there is no communication between the trachea and the oesophagus. After such an operation, the patient is unable to talk. In order to allow the patient to recover some vocal function, it is known to surgically create a hole, or fistula, between the trachea and the oesophagus. When the patient desires to talk, the patient covers the stoma at the outside of the throat with a finger so that air from the lungs is directed from the trachea into the oesophagus and speech can be created in a manner which is broadly similar to normal speech. However, the fistula has the potential of allowing food or liquid to pass from the oesophagus into the trachea, and this is clearly undesirable. In order to prevent passage of food or liquid into the trachea, it is known to insert a speech valve into the fistula between the oesophagus and the trachea.

A speech valve acts as a one way valve which closes to prevent food and liquid passing from the oesophagus into the trachea, but which can be opened by air pressure when the stoma at the outside of the throat is covered and the patient is breathing out. In this way, the patient is able to generate speech while the valve prevents ingress of food and liquid into the trachea. Known speech valves are made of silicone rubber. Most known designs have a hollow cylindrical body which is provided at each end with a radially extending annular flange. The cylindrical body fits within the fistula with one flange lying in the trachea and the other flange lying in the oesophagus. The flanges hold the valve in place in the fistula while the resilience of the silicone material allows the valve to be inserted into the fistula, by resilient flexing of at least one of the flanges. The valve also has a closure member in the form of a flap which may be provided either at one end of the valve or internally within the cylindrical body.

Known speech valves work well initially, but their function rapidly deteriorates, often in as little as three months from insertion. There is little if any deterioration of the silicone rubber material of the valve. Instead, function degrades due to the build up of biofilm, including bacteria, on the surfaces of the valve. This biofilm build up may prevent the valve from closing properly, in which case food and liquid may enter into the trachea, or it may make opening of the valve more difficult in which case speech becomes difficult. Once function of the valve is impaired, it is necessary to replace the valve.

In accordance with a first aspect of the invention, there is provided a speech valve having a body and a projection, the body being at least partially insertable into a fistula between the trachea and the oesophagus so as to provide a closable passage between the trachea and the oesophagus with the projection lying outside the fistula to resist passage of the valve through the fistula, the valve having a seat and a closure member which are movable relative to one another between an open position and a closed position in which a closure surface of the seat contacts a closure surface of the closure member so as to close the valve and thereby close the passage between the trachea and the oesophagus, the closure surfaces being sufficiently rigid to prevent substantial flexing during operation.

In accordance with a second aspect of the invention, there is provided a speech valve having a body and a projection, the body being at least partially insertable into a fistula between the trachea and the oesophagus so as to provide a closable passage between the trachea and the oesophagus with the projection lying outside the fistula to resist passage of the valve through the fistula, the body having a seat and the valve including a closure member which is movable between an open position and a closed position in which the closure member contacts the seat so as to close the valve and thereby close the passage between the trachea and the oesophagus, the body and the closure member having respective guidance surfaces which slidingly contact one another to guide the closure member between the open and the closed positions so that the sliding contact tends to clean the guidance surfaces.

In accordance with a third aspect of the invention, there is provided a speech valve having a body and a projection, the body being at least partially insertable into a fistula between the trachea and the oesophagus so as to provide a closable passage between the trachea and the oesophagus with the projection lying outside the fistula to resist passage of the valve through the fistula, the valve including a closure member which moves relative to the body between an open position in which said passage is open and a closed position in which said passage is closed by contact between the body and the closure member, each one of the body and the closure member being made of a ceramic material.

The following is a more detailed description of embodiments of the invention, by way of example, reference being made to the appended drawings in which.

Figure 1:
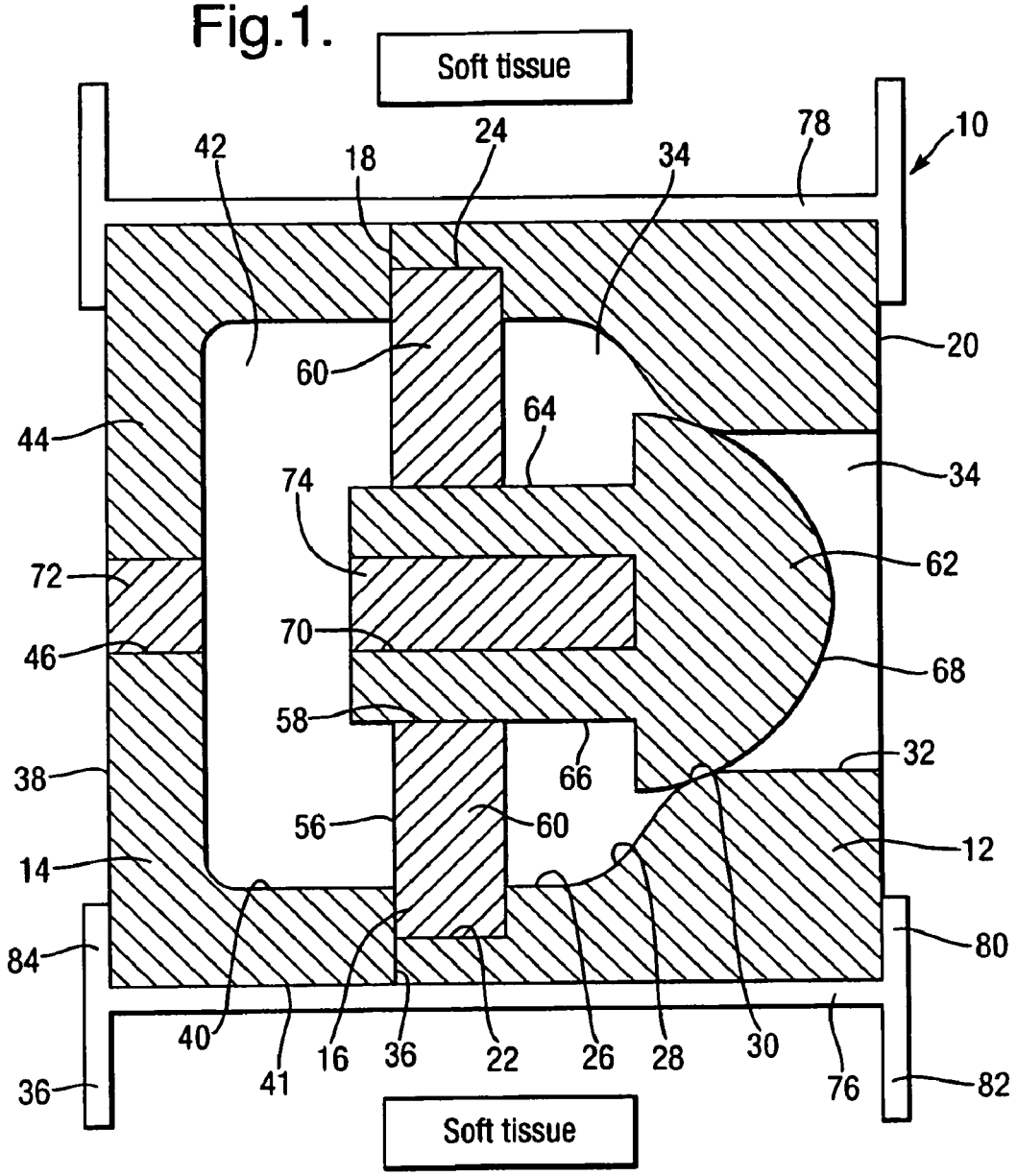
FIG. 1 is a schematic, cross-sectional diagram of a speech valve.
Figure 2:
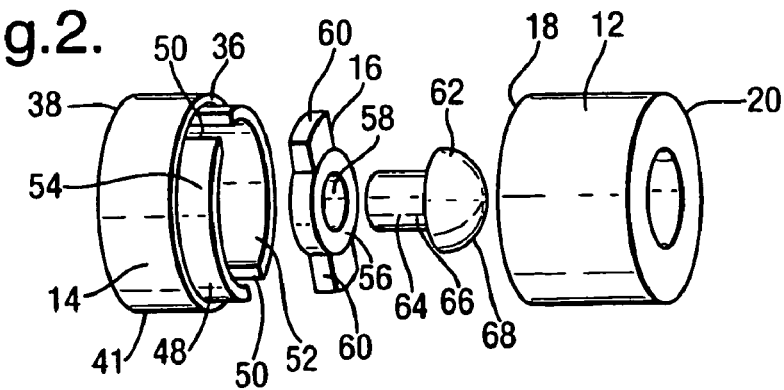
FIG. 2 is an exploded, perspective view of the body and the closure member of the speech valve of FIG. 1.

Referring to FIGS. 1 and 2, the speech valve 10 has a body which consists of a first generally cylindrical member 12, a second generally cylindrical member 14, and a guidance member 16.

Referring to FIG. 1, the first generally cylindrical member 12 has an inner end 18 and an outer end 20. The inner end 18 and the outer end 20 are connected by an inner surface. Starting from the inner end 18, the inner surface has a first cylindrical portion 22 which extends to a radially inwardly extending step portion 24. The radially inwardly extending step portion 24 joins a second cylindrical portion 26 which extends to an arcuate portion 28. The arcuate portion 28 extends inwardly to a spherical seat portion 30. The seat portion 30 joins a third cylindrical portion 32 which extends to the outer end 20 of the first cylindrical member 12. As seen in FIG. 1, the inner surface of the first cylindrical member 12 defines a passageway 34 through the first cylindrical member 12.

The second generally cylindrical member 14 has an inner end 36 and an outer end 38. The inner end 36 and the outer end 38 are connected by a inner cylindrical surface 40 and a outer cylindrical surface 41. The inner cylindrical surface 40 defines a passageway 42 which extends through the second generally cylindrical member 14. At the outer end 38, the second generally cylindrical member 14 is provided with a cross-brace 44 which extends diametrically across the second cylindrical member 14 but which does not close the passageway 42. The cross-brace 44 is provided with an aperature 46 located on the axis of the second cylindrical member 14.

As seen in FIG. 2, the second generally cylindrical member 14 is provided with a flange 48 which extends axially from the inner end 36 of the second cylindrical member 14. The flange 48 is generally annular but is interrupted by two diametrically opposed gaps 50. The flange 48 has an inner cylindrical surface 52 which is continuous with the inner cylindrical surface 40 of the second cylindrical member 14. The flange 48 also has an outer cylindrical surface 54 which, as seen in FIG. 2, lies radially inwardly of the outer cylindrical surface 41 of the second cylindrical member 14.

The guidance member 16 has a central annular portion 56 which is provided with an inner cylindrical guidance surface 58. Two diametrically opposed tabs 60 extend radially outwardly from the annular portion 56.

The speech valve 10 also includes a closure member 62. The closure member 62 has a cylindrical stem 64 provided with an outer cylindrical guidance surface 66. Additionally, the closure member 62 also has a hemispherical head 68. The radius of curvature of the hemispherical head 68 of the closure member 62 matches the radius of curvature of the spherical seat portion 30 of the inner surface of the first cylindrical member 12. As seen in FIG. 1, the cylindrical stem 64 of the closure member 62 is provided with an aperature 70.

The first cylindrical member 12, the second cylindrical member 14, the guidance member 16 and the closure member 62 are preferably all made of the same ceramic material. One ceramic material which has been found to be highly suitable is partially stabilised zirconia (PSZ). All of the surfaces of the first cylindrical member 12, the second cylindrical member 14, the guidance member 16 and the closure member 62 are manufactured to a high degree of smoothness.

As shown in FIG. 1, a first magnet 72 is fixed in the aperature 46 in the cross-brace 44 of the second cylindrical member 14. A second magnet 74 is fixed in the aperature 70 of the closure member 62. The first and second magnets 72, 74 may be coated in a suitable bio-compatible material such as Teflon (Trade Mark), or silicone rubber.

In order to assemble the body 12, 14, 16 and the closure member 62 of the speech valve 10, the cylindrical stem 64 of the closure member 62 is inserted into the inner cylindrical guidance surface 58 of the guidance member 16. The outer cylindrical guidance surface 66 of the closure member 62 is a close sliding fit within the inner cylindrical guidance surface 58 of the guidance member 16.

The guidance member 16 with the closure member 62 inserted therein is then assembled with the second cylindrical member 14 so that each one of the two tabs 60 provided on the guidance member 16 is received within a respective one of the two gaps 50 provided in the flange 48 of the second cylindrical member 14.

Finally, the second cylindrical member 14, carrying the guidance member 16 and the closure member 62, is assembled with the first cylindrical member 12. In order to do this, the flange 48 of the second cylindrical member 14 is inserted into the inner end 18 of the first cylindrical member 12 so that the outer cylindrical surface 54 of the flange 48 fits tightly within the first cylindrical portion 22 of the inner surface of the first cylindrical member 12 and the flange 48 abuts the radially extending step portion 24 of the inner surface of the first cylindrical member 12. The first and second cylindrical members 12, 14 may be permanently fixed together using a suitable bio-compatible adhesive or any other suitable method.

As seen in FIG. 1, when assembled, the guidance member 16 is held firmly between the first and second cylindrical members 12, 14 with the tabs 60 located in the gaps 50. The closure member 62 is held within the inner cylindrical guidance surface 58 of the guidance member 16 and is able to slide in an axial direction. As seen in FIG. 1, the passageway 34 extending through the first cylindrical member is now continuous with the passageway 42 extending through the second cylindrical member 14 so as to create a passageway extending from the outer end 38 of the second cylindrical member 14 to the outer end 20 of the first cylindrical member 12. This will be referred to as the valve passageway.

The first and second magnets 72, 74 are orientated so that they repel one another, tending to move the closure member 62 into the position shown in FIG. 1.

FIG. 1 shows the closure member 62 in a closed position. In this position, the hemispherical head 68 of the closure member 62 lies in sealing contact against the spherical seat portion 30 of the first cylindrical member 12 so as to close the valve passageway. However, when a positive pressure is applied to the outer end 20 of the first cylindrical member 12, the closure member 62 slides (in a right to left direction when the speech valve is orientated as shown in FIG. 1) against the magnetic force provided by the magnets 72, 74, so that the hemispherical head 68 moves away from the spherical seat portion 30 so as to open the valve passageway.

As shown in FIG. 1, the speech valve 10 is also provided with a sleeve 76 which is formed from silicone rubber. The sleeve 76 has a central cylindrical portion 78 which is provided, respectively, with both inwardly and outwardly radially extending flanges at each end. A first inwardly extending annular flange 80 lies closely against the outer end 20 of the first cylindrical member 12. The first inwardly extending flange 80 is continuous with a first outwardly extending flange 82. At the other end of the sleeve 76 a second inwardly extending flange 84 lies closely against the outer end 38 of the second cylindrical member 14. This second inwardly extending flange 84 is continuous with a second outwardly extending flange 86. The first and second inwardly extending flanges 80, 84 hold the valve body 12, 14, 16 within the cylindrical portion 78 of the sleeve 76.

In use, this speech valve 10 is inserted into a fistula between the trachea and the oesophagus with the outer end 20 of the first cylindrical member 12 lying at the trachea side and the outer end 38 of the second cylindrical member 14 lying at the oesophageal side. The first outwardly extending annular flange 82 lies outside the fistula within the trachea and the second outwardly extending annular flange 86 also lies outside the fistula within the oesophagus. In this way, the two outwardly extending annular flanges 82, 86 hold the speech valve 10 firmly in place in the fistula between the oesophagus and the trachea. The outwardly extending annular flanges 82, 86 also help to prevent fluid and particles from escaping between the speech valve 10 and the fistula into the trachea.

The flexible nature of the outwardly extending annular flanges 82, 86 allows the speech valve 10 to be inserted into the fistula.

When the patient does not wish to speak, air passes into the trachea via the stoma at the outside of the patient's throat and is also expelled from the lungs through the stoma in the same way. The closure member 62 is in the closed position shown in FIG. 1 and this prevents food or liquid passing from the oesophagus into the trachea.

When the patient wishes to speak, the patient usually uses a finger or thumb to close the stoma at the outside of the patient's throat. Now, when the patient breathes out, the air pressure in the trachea raises and this opens the speech valve 10 by forcing the closure member 62 to the left (as shown in FIG. 1) against the magnetic force exerted by the magnets 72, 74. Air from the trachea can then pass through the speech valve 10 into the oesophagus and can be used to form speech. When the patient has finished talking, the finger or thumb is removed from the stoma, the air pressure in the trachea reduces, and the closure member 62 is forced into the closed position shown in FIG. 1 by the magnetic repulsion.

It has been found that the surfaces of the components formed from partially stabilised zirconia (the first and second generally cylindrical members 12, 14, the guidance member 16 and the closure member 62) are highly resistant to the growth of biofilm. This is believed to reflect an inherent resistance, exhibited by the ceramic material, to the growth of biofilm. Also the repeated action of making contact between the hemispherical head 68 and the spherical seat portion 30 of the first cylindrical member 12, in combination with the rigid nature of the ceramic material may help to clean the contacting surfaces. Additionally, it is believed that the sliding movement between the outer cylindrical guidance surface 66 of the closure member 62 and the inner cylindrical guidance surface 58 of the guidance member 16 tends to clean debris, and prevent the formation of biofilm on these guidance surfaces.

Additionally, as seen in FIG. 1, all of the internal corners within the speech valve 10 are rounded. An internal corner is defined as the meeting between two surfaces which extend, relative to one another, at an angle of less than 180°. Thus, for example, looking at FIG. 1, the corner between the cross-brace 42 and the inner cylindrical surface 40 of the second cylindrical member 14 is rounded. Another rounded corner can be found at the arcuate portion 28 of the inner surface of the first cylindrical member 12. It is believed that the rounding of internal corners helps to prevent the accumulation of biofilm. This may be because gas flow through the speech valve 10, such as when the patient coughs, tends to dislodge any biological material which has accumulated within the speech valve 10. In this way, the speech valve 10 tends to be self-cleaning. It is believed that the smooth surfaces of the ceramic materials help this process.

It will be appreciated that the speech valve may not be as described above and many variations may be made without departing from the current invention.

Firstly, the body of the speech valve 10 and the closure member 62 need not be made from partially stabilised zirconia. Any suitable material may be used. Generally, a suitable material will be hard, rigid, chemically inert and non-porous. One class of materials which is believed to be suitable is ceramics. An alternative suitable ceramic is alumina.

Alternatively, the body of the speech valve 10 and the closure member 62 may be formed of a rigid material which is not itself particularly resistant to the formation of biofilm, but these components may be provided with a coating which is resistant to the formation of biofilm. For example, rigid material may be coated with a coating such as diamond-like carbon coating.

The speech valve body and the closure member need not have the configuration described above and shown in the figures. Any suitable valve configuration may be used. In one alternative configuration, the closure member 62 may rotate as it moves axially between a closed and open position. Rotational movement of the closure member relative to the speech valve body may help to keep the closure surfaces and the guidance surfaces clean.

Figure 3:
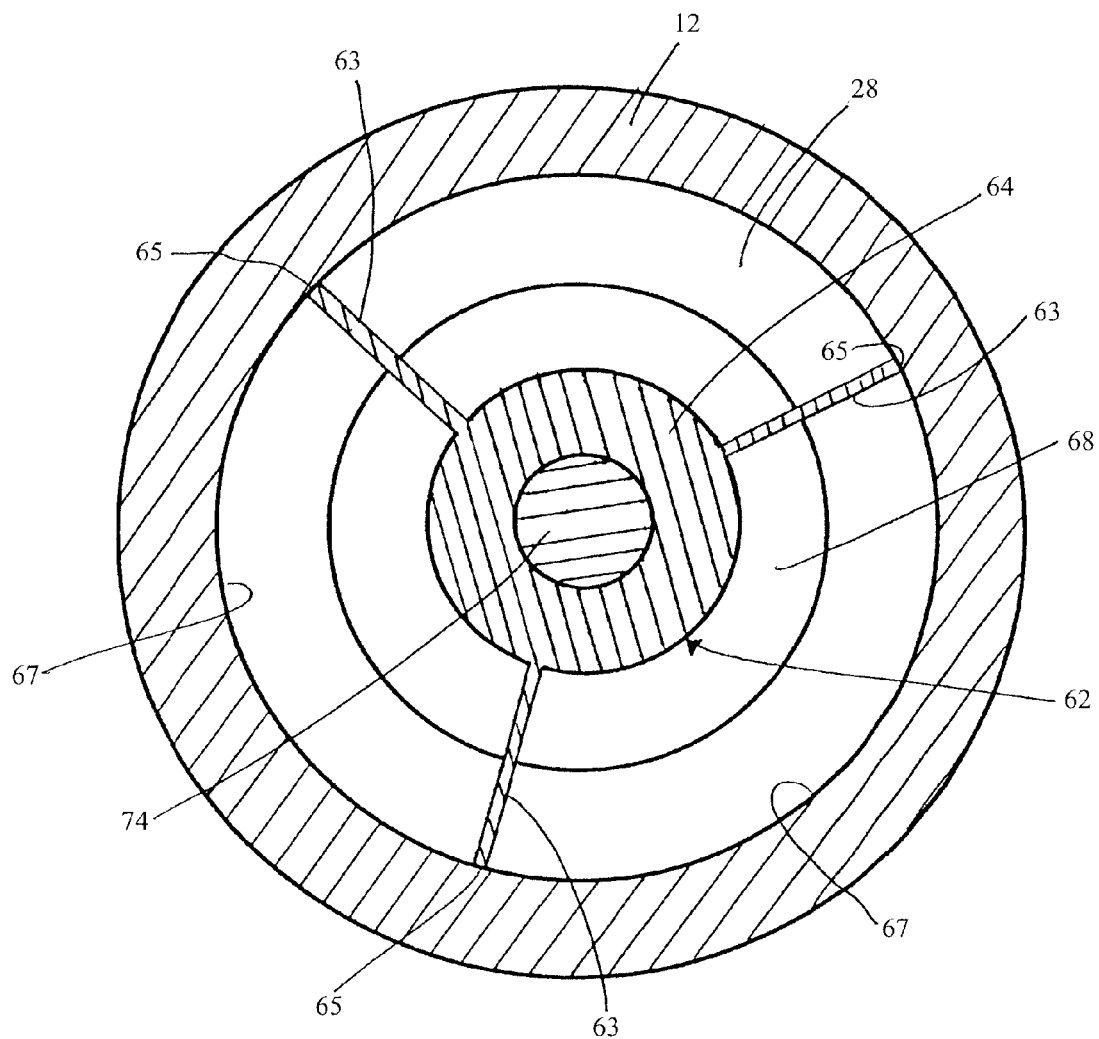
FIG. 3 is a schematic, cross-sectional diagram of an alternative embodiment of the speech valve.

FIG. 3 shows an alternative embodiment of the speech valve. In FIG. 3, features of the speech valve which correspond to features of FIGS. 1 and 2 are given the same reference numerals and are not described in detail. In the alternative embodiment of FIG. 3, the guidance member 16 is dispensed with. The closure member 62 has a plurality of angularly spaced fins 63 extending radially outwardly from the stem 64. Each fin has an outer end surface 65, the outer end surfaces 65 collectively forming a guidance surface which slides relative to an inner annular guidance surface 67 of the valve body 12, 14. In this arrangement, gas can pass freely between the angularly spaced fins 63.

In the speech valve 10 described above and shown in FIG. 1, the speech valve is provided with two radially outwardly extending annular flanges 82, 86. Both of these outwardly extending flanges 82, 86 are formed of the resilient material silicone rubber. However, one outwardly extending flange may be formed of a material, such as ceramic, which is more resistant to the growth of biofilm. This flange need not be resilient. So long as the other one of the flanges is resilient, it should still be possible to insert the speech valve into the fistula between the trachea and the oesophagus.

Instead of using the magnets 72, 74 other means, such as a spring, may be used to bias the closure member 62 towards the spherical seat portion 30.

The invention claimed is:

1. A speech valve having a body and a projection, the body being at least partially insertable into a fistula between the trachea and the oesophagus so as to provide a closable passage between the trachea and the oesophagus with the projection lying outside the fistula to resist passage of the valve through the fistula, the body having a seat and the valve including a closure member which is movable between an open position and a closed position in which the closure member contacts the seat so as to close the valve and thereby close the passage between the trachea and the oesophagus, the closure member having a stem and a plurality of mutually angularly spaced fins extending outwardly from the stem, the body having a guidance surface, the fins of the closure member having respective outer edges which form a guidance surface of the closure member, the guidance surface of the body and the outer edges of the fins slidingly contacting one another to guide the closure member between the open and the closed positions so that the sliding contact tends to clean the guidance surfaces.

2. A speech valve according to claim 1, wherein the guidance surfaces are sufficiently rigid to prevent substantial flexing during operation.

3. A speech valve having a body and a projection, the body being at least partially insertable into a fistula between the trachea and the oesophagus so as to provide a closable passage between the trachea and the oesophagus with the projection lying outside the fistula to resist passage of the valve through the fistula, the body having a seat and the valve including a closure member which is movable between an open position and a closed position in which the closure member contacts the seat so as to close the valve and thereby close the passage between the trachea and the oesophagus, the body and the closure member having respective guidance surfaces which slidingly contact one another to guide the closure member between the open and the closed positions so that the sliding contact tends to clean the guidance surfaces, wherein each said surface is provided by diamond-like carbon coating.

4. A speech valve according to claim 1, wherein the projection is resilient so as to allow the projection to be flexed so as to be passed through the fistula.

5. A speech valve according to claim 1, wherein the body has first and second ends, the projection being provided at one of the ends and a further projection being provided at the other one of the ends.

6. A speech valve according to claim 5, wherein the further projection is resilient.

7. A speech valve according to claim 4, wherein a resilient sleeve is provided around the body, the projection being integral with the sleeve.

8. A speech valve according to claim 7, wherein the sleeve is made of silicone rubber.

9. A speech valve according to claim 1, wherein the closure member is biased towards the closed position.

10. A speech valve according to claim 9, wherein said bias is achieved by magnetic force.

11. A speech valve according to claim 1, in which all internal corners are rounded to resist accumulation of biological material.

12. A speech valve having a body and a projection, the body being at least partially insertable into a fistula between the trachea and the oesophagus so as to provide a closable passage between the trachea and the oesophagus with the projection lying outside the fistula to resist passage of the valve through the fistula, the body having a seat and the valve including a closure member which is movable between an open position and a closed position in which the closure member contacts the seat so as to close the valve and thereby close the passage between the trachea and the oesophagus, the body and the closure member having respective guidance surfaces which slidingly contact one another to guide the closure member between the open and the closed positions so that the sliding contact tends to clean the guidance surfaces, and wherein the closure member rotates relative to the body as it moves axially between the open and closed positions.

13. A speech valve having a body and a projection, the body being at least partially insertable into a fistula between the trachea and the oesophagus so as to provide a closable passage between the trachea and the oesophagus with the projection lying outside the fistula to resist passage of the valve through the fistula, the body having a seat and the valve including a closure member which is movable between an open position and a closed position in which the closure member contacts the seat so as to close the valve and thereby close the passage between the trachea and the oesophagus, the body and the closure member having respective guidance surfaces which slidingly contact one another to guide the closure member between the open and the closed positions so that the sliding contact tends to clean the guidance surfaces, and wherein the closure member is biased towards the closed position by a repulsive magnetic force.

14. A speech valve having a body and a projection, the body being at least partially insertable into a fistula between the trachea and the oesophagus so as to provide a closable passage between the trachea and the oesophagus with the projection lying outside the fistula to resist passage of the valve through the fistula, the valve including a closure member which moves relative to the body between an open position in which said passage is open and a closed position in which said passage is closed by contact between the body and the closure member, the closure member having a stem and the body having an inner annular guidance surface, wherein each one of the body and the closure member is made of a ceramic material, wherein a plurality of angularly spaced fins extend radially outwardly from the stem, each fin having an outer end surface, the outer end surfaces of the fins collectively forming a guidance surface, the outer end surfaces of the fins slidingly contacting the inner annular guidance surface of the body to guide the closure member between the open and closed positions, the arrangement being such that gas can pass freely between the angularly spaced fins.

* * * * *